United States Patent [19]

Matsuno et al.

[11] Patent Number: 5,282,860
[45] Date of Patent: Feb. 1, 1994

[54] STENT TUBE FOR MEDICAL USE

[75] Inventors: Kiyotaka Matsuno; Katsushi Watanabe, both of Tokyo, Japan

[73] Assignee: Olympus Optical Co., Ltd., Tokyo, Japan

[21] Appl. No.: 958,003

[22] Filed: Oct. 8, 1992

[30] Foreign Application Priority Data

Oct. 16, 1991 [JP] Japan .................. 3-266691

[51] Int. Cl.⁵ .............................. A61F 2/04
[52] U.S. Cl. .......................... 623/12; 623/1; 623/11
[58] Field of Search ............ 623/1, 11, 12; 606/194

[56] References Cited

U.S. PATENT DOCUMENTS 3,272,204  9/1966  Artandi et al. ............... 623/1
4,546,500 10/1985  Bell .............................. 623/12
4,657,024  4/1987  Coneys .
5,163,951 11/1992  Pinchuk et al. ............... 623/1

FOREIGN PATENT DOCUMENTS 1-152636 10/1989  Japan .

*Primary Examiner*—David Isabella
*Assistant Examiner*—Debra S. Brittingham
*Attorney, Agent, or Firm*—Frishauf, Holtz, Goodman & Woodward

[57] ABSTRACT

A stent tube comprises an inner tube and an outer tube with a reinforcing braided member fitted between the inner tube and the outer tube. The inner tube is made of a fluorine-based resin. The stent tube is hard to clog at its inner wall and has a strength enough great for a bending force.

9 Claims, 4 Drawing Sheets

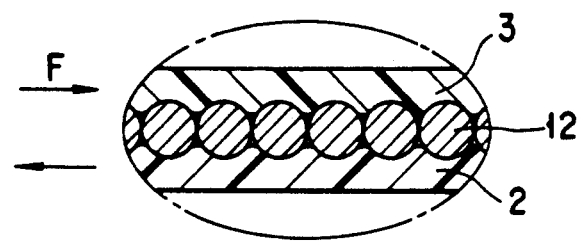
F I G. 4
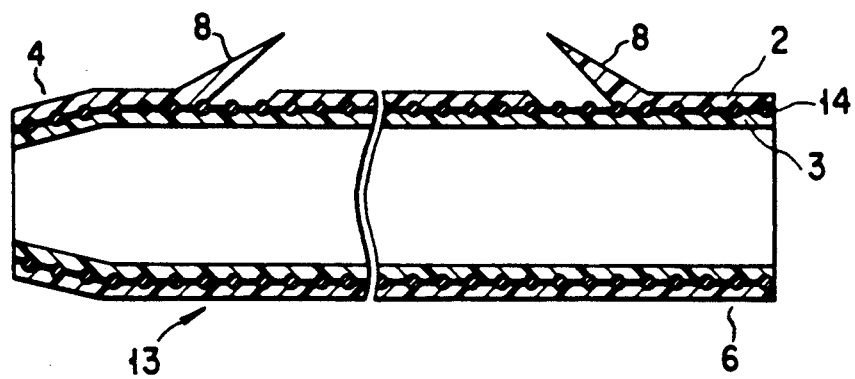
F I G. 5
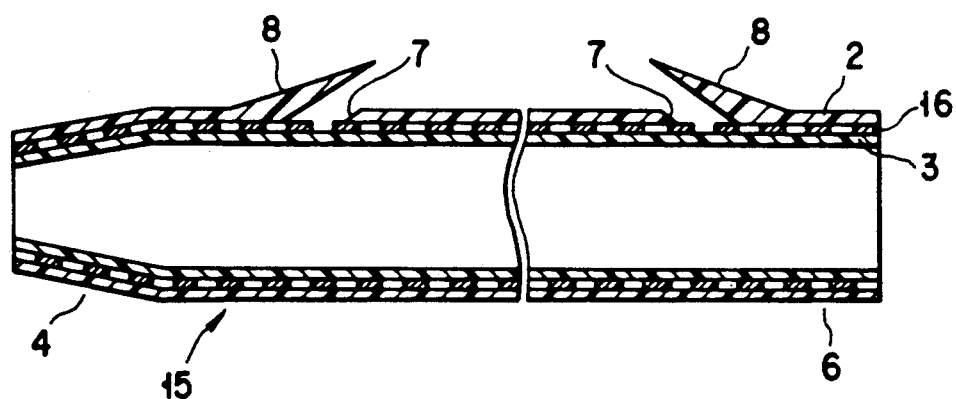
F I G. 6

STENT TUBE FOR MEDICAL USE

BACKGROUND OF THE INVENTION

1. Field of the Invention

The present invention relates to a stent tube adapted to be placed in a body cavity of a human subject so as to drain, for example, a body fluid.

2. Description of the Related Art

Published Unexamined Japanese Utility Model Application 1-152636, for example, discloses a stent tube (hereinafter referred to a drainage tube) adapted to be placed in a human body to provide a passage for draining a body fluid, etc. In general, this type of drainage tube is formed of, for example, a polyethylene tube and, therefore, a poor frictional resistance and separation are involved. Thus the tube is liable to be clogged.

The drainage tube of the aforementioned Utility Model Application has a fluorine-based resin layer formed on its inner surface. FIG. 10 shows a practical arrangement of that drainage tube.

That is, the drainage tube 1 has a double-layered structure comprising an outer tube 2 made of polyethylene tube and an inner tube 3 made of a fluorine-based resin layer. The forward end 4 of drainage tube 1 has a tapering section 5 which is decreased in diameter toward its forward edge. A pair of cut areas 7,7 are provided one at the forward end portion and one at the rear end portion of the drainage tube 1 such that the cut areas 7,7 are inclined gradually toward the end edges of the drainage tube to provide a pair of openable/closable side flaps 8,8 there.

The aforementioned tube structure involves various drawbacks. First, the inner tube 3 in the double-layered structure is made of a fluorine-based resin and is more rigid than the outer tube 2 made of polyethylene, thus making the drainage tube 1 rigid as a whole. As one solution to this problem, if the outer tube 2 is made thinner, then a resultant pair of side flaps on the outer tube 2 becomes thinner, thus prominently lowering the ability with which the side flaps 8 are anchored on the body cavity of a human subject.

When the drainage tube 1 is inserted into the human body cavity through a channel of an endoscope, the drainage tube 1 passes through a forceps-raising base section. At that time, the drainage tube, if a thinner tube is used as the inner tube 3, is bent at the location of the forceps-raising base section, causing the bending of the inner tube 3 and the consequent collapsing of the inner tube 3. The collapsing of that tube is more liable to occur at the cut areas 7 providing the side flaps 8.

Second, if an inner tube 3 made of a fluorine-based resin is formed inside an outer tube 2 made of polyethylene so as to secure the same inner and outer diameters as those of a single ordinary drainage tube, it follows that the thickness of the outer tube 2 is thinned by the extent that the inner tube 3 is provided. Further, a contrast medium is mixed in the outer tube 2 so that the outer tube 2 is observable by an X-ray, but, in this case, the contrast medium in the outer tube 2 does not adequately secure its purpose. If, on the other hand, a contrast medium is mixed in the inner tube 3 made of a fluorine-based resin, a greater frictional resistance is involved so that the drainage tube fails to serve its own purpose fully.

Third, it is very difficult to make cut areas, as side flaps, in a relatively thin, outer tube 2 only. In this case it is necessary to initially insert an inner tube 3 of a fluorine-based resin into an outer tube and fix it there so that cut areas are provided as side flaps, etc. Upon assembly of a drainage tube by inserting the inner tube 3 into the outer tube 2, buckling is liable to occur at the cut areas of the outer tube 2. As a result, the drainage tube is difficult to manufacture and cannot be manufactured at low costs.

SUMMARY OF THE INVENTION

It is accordingly the object of the present invention to provide a stent tube usable in a human body cavity, which is hard to bend and lower in cost and, in addition, hard to clog at an inner wall of the tube.

In order to achieve the aforementioned object, a stent tube for use in a body cavity of a human being is provided which comprises an outer tube, an inner tube made of a fluorine-based resin, and a reinforcing member fitted between the outer tube and the inner tube. Thus the stent tube is hard to clog at its inner wall and has a mechanical strength enough hard to bend.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4 shows cross-sectional tube, enlarged at an area B in the embodiment of FIG. 2;

FIG. 5 shows a cross-sectional view showing a stent tube, for use in a human body cavity, according to a third embodiment of the present invention;

FIG. 6 shows a cross-sectional view, for use in a human body cavity, according to a fourth embodiment of the present invention;

DETAILED DESCRIPTION OF THE PREFERRED EMBODIMENTS

Figure 1:
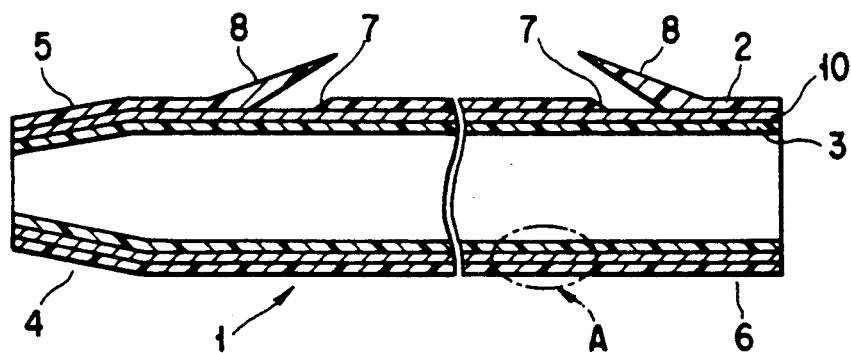
FIG. 1 shows a cross-sectional view showing a stent tube, for use in a human body cavity, according to a first embodiment of the present invention.
Figure 2:
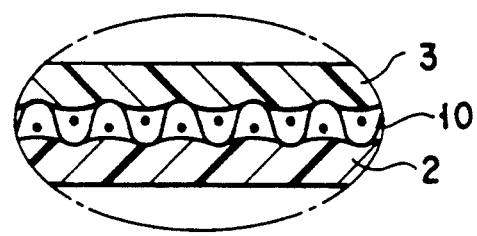
FIG. 2 shows cross-sectional view, enlarged at an area A in the embodiment of FIG. 1.

FIGS. 1 and 2 show a first embodiment of the present invention. As shown in FIGS. 1 and 2, a stent tube 1

(hereinafter referred to as a drainage tube) comprises an outer tube 2 and an inner tube 3 with a braided member 10 fitted, as a reinforced, cylindrical member, between the outer tube 2 and the inner tube 3. The braided member 10 is comprised of a fine wire-braided mesh structure. The inner tube 2 is made of a fluorine-based resin, such as a fluorinated ethylenepropylene copolymer (Tefron—a trade name). The outer tube 3 is made of a synthetic resin, such as polyethylene, containing a contrast medium. The member 10 is so multi-indented or undulated as to be set in biting engagement with the adjacent tubes 2 and 3. As a result, it is possible to achieve a firm contact force with which the member 10 is set in contact with the adjacent tubes 2 and 3.

A cylindrical tapering section 5 is provided at a forward end 4 side such that it is decreased in diameter toward the forward end 4 of the tube 1. A pair of side flaps 8,8 are provided one at the forward end 4 side and one at the rear end 6 side such that their tip ends extend toward each other with a spacing left therebetween at an intermediate area of the drainage tube 1. Inclined cut areas 7 and 7 are provided at the outer surface of the drainage tube and gradually inclined away from each other one toward the forward end 4 side and one toward the rear end 6 side at a location between the side flaps 8 and 8. This specific arrangement enables the side flaps 8 and 8 to be openable/closable relative to the inclined cut areas 7 and 7. It is to be noted that the cut areas 7 and 7 are formed in the outer tube 2 only, not in the member 10 and inner tube 3.

The operation of the drainage tube 1 will be explained below.

The drainage tube 1, when being inserted into a body cavity of a human being, is passed through a channel (insertion channel) of an endoscope, not shown, into a human body duct and placed in the duct, for example, passed through the duodinal papilla 17 into the general bile duct of a human subject and placed at the narrow portion of the duct. At this time, the drainage tube 1 is positively held, by the anchoring action of the side flaps 8, at the narrow portion of the general bile duct 18 and provides a passage at that narrow portion of the duct, allowing the bile to be discharged from the general bile duct 18.

According to the drainage tube 1 of the present invention, the inner tube 3 is made of a fluorinated ethylenepropylene copolymer and much less frictional resistance is involved at the inner surface of the drainage tube 1. As a result, a foreign substance, such as germs and cholesterols, is less liable to be deposited on the inner surface of the drainage tube and, even if being deposited there, is readily separable from the inner surface of the drainage tube due to its self-lubrication quality so that the foreign substance such as the germs and cholesterols is readily separable from the inner surface of the drainage tube 1.

It is thus possible to prevent clogging of the drainage tube 1, that is, the inner tube 3, by such a foreign substance. Further, since no edge is formed, by the cut areas 7, at the inner portion of the drainage tube 1, there is less chance of the inner tube being clogged.

Further, since the braided member 10 is provided between the outer tube 2 and the inner tube 3, it provides an added strength to the resultant tube 1 and the inner surface of the drainage tube 1 is not collapsed upon being received from a bending force. There is no risk that the drainage tube 1 will be excessively bent even if the inner tube 3 is practically so thin as possible.

It is thus possible to thicken the outer tube 2 by that thickness extent. In addition, the side flaps 8 can also be reasonably so thickened as to provide a firm, adequate force of anchoring to the inner portion of the duct of the human being.

The reinforced member 10 is braided with the fine wires and, together with the contrast medium-mixed outer tube 2, provides an adequate density of contrast. A length of the three-layered tube comprising tubes 2 and 3 and member (tube) 10 is cut to given segments and side flaps 8 can be formed as will be set out below. The member 10, being fitted between the inner and outer tubes 2 and 3, serves as a stopper when the cut areas 7 and 7 are formed by a cutter, etc., so as to provide the aforementioned side flaps 8. That is, the cut areas 7 can be formed only the outer tube 2 and the side flaps 8 can be formed without injuring the inner tube 3.

Figure 3:
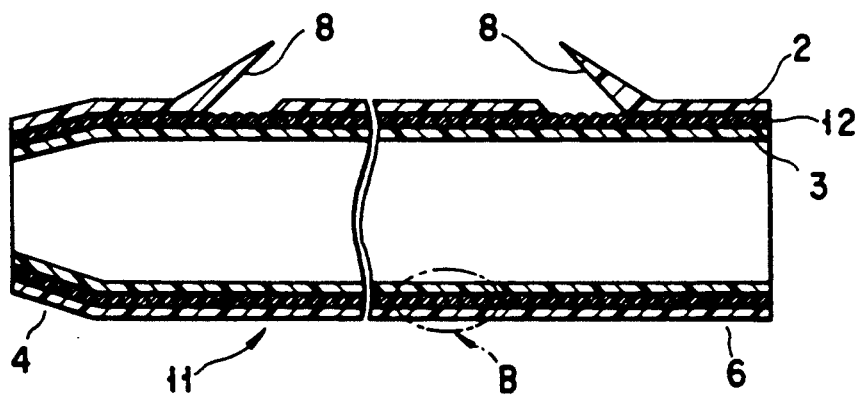
FIG. 3 shows cross-sectional view showing a stent tube, for use in a human body cavity, according to a second embodiment of the present invention.

FIGS. 3 and 4 show a drainage tube according to a second embodiment of the present invention. As shown in these Figures, the drainage tube 11 has outer and inner tubes 2 and 3, as in the first embodiment, with a coil 12 of a compactly or tightly wound metal wire provided, as a reinforced member of a substantially cylindrical configuration, between the outer tube 2 and the inner tube 3. The second embodiment is similar to the first embodiment except that the compact metal wire coil is arranged between the inner tube 2 and the outer tube 3. This drainage tube can be used in the same manner as the preceding drainage tube. The drainage tube 12 of the second embodiment may be so constructed that a plurality of wires are compactly wound into a coil.

The second embodiment can perform the same function as that of the first embodiment and has an added function as will be set out below. Since the compact coil 12 is disposed between the outer tube 2 and the inner tube 3, the multi-indented area of the compact coil 12 is set in biting contact with the inner surface portions of the adjacent tubes 2 and 3 as shown in FIG. 4. By this engaging means it is possible to achieve a firm force of engagement between the outer tube 2 and the inner tube 3. The respective tubes 2 and 3 are prevented from being displaced even if they receive an external force F tending to be displaced in an axial direction as indicated by arrows in FIG. 4. It is thus possible to prevent a displacement of the inner tube 3 out of the outer tube 2.

As set out above, the drainage tube 11 is inserted through the endoscope's channel into the body cavity of the human being. In this case, the rear end 6 of the drainage tube 11 is forwardly pushed by a pushing member, not shown, and, even when, at this time, an external axial force F as shown in FIG. 4 is applied to the rear end of the drainage tube 11, the inner tube 3 firmly stays as it is relative to the outer tube 3.

FIG. 5 shows a drainage tube according to a third embodiment of the present invention. As shown in FIG. 5, the drainage tube 13 comprises an outer tube 2, an inner tube 3 and a fine-wire coil 14 wound in a coarse pitch into a cylindrical configuration and disposed, as a reinforcing member, between the outer tube 2 and the inner tube 3. The third embodiment is similar to the preceding other embodiments except that the coil 14 is wound, in the coarse pitch, into a cylindrical configuration. The third embodiment is used in the same manner as set out in connection with the preceding embodiments.

The third embodiment performs the same function as that of the preceding embodiments and has an advantage as will be set out below. The drainage tube 13 of the third embodiment has the coarsely wound coil 14 disposed between the outer tube 2 and the inner tube 3 and is, therefore, difficult to collapse and flexible in nature throughout the whole length. The flexibility of the drainage tube 13 throughout the whole length can properly be adjusted by varying the extent of winding of the coil from tight to coarse. Further, it is possible to provide a different flexibility to some area or areas of the drainage tube by partially varying the manner of winding of the coil 14. It is thus possible to properly place the drainage tube 13 along the inner surface of the duct of the human being and hence to alleviate the pain of the patient.

Figure 7:
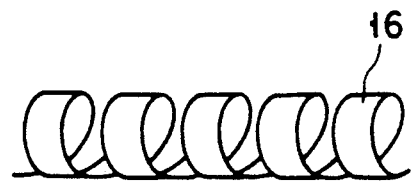
FIG. 7 shows a cross-sectional view showing a flexible metal ribbon in the embodiment of the present invention.

FIGS. 6 to 9 show a drainage tube according to a fourth embodiment of the present invention. The drainage tube 15 comprises an outer tube 2 and an inner tube 3 as shown in FIG. 6 and further comprises a thin metal ribbon or flexible ribbon 16 spirally wound into a cylindrical configuration as shown in FIG. 7 and disposed, as a reinforcing member, between the outer tube 2 and the inner tube 3. The fourth embodiment is the same as the preceding embodiments except that the ribbon 16 is disposed between the inner tube 2 and the outer tube 3. The fourth embodiment is used in the same manner as set out in connection with the first embodiment.

Figure 8:
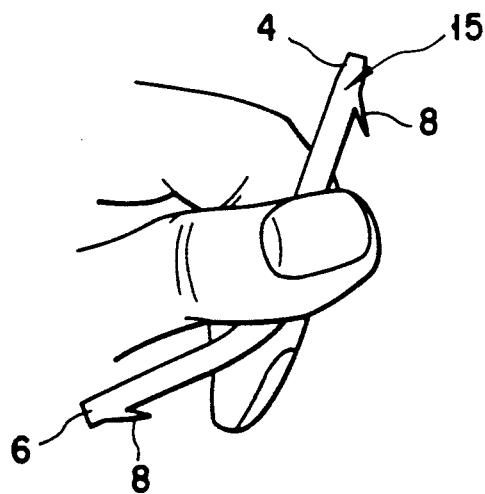
FIG. 8 shows an explanative view for imparting a bending habit to the present stent tube by fingers.
Figure 9:
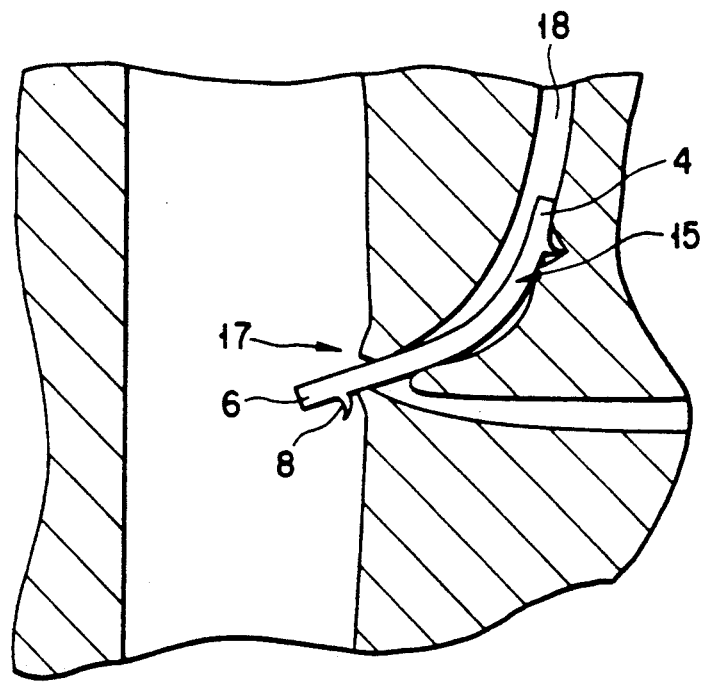
FIG. 9 shows an explanative view showing the present stent tube as inserted via the duodinal papilla into the common bile duct and placed there.
Figure 10:
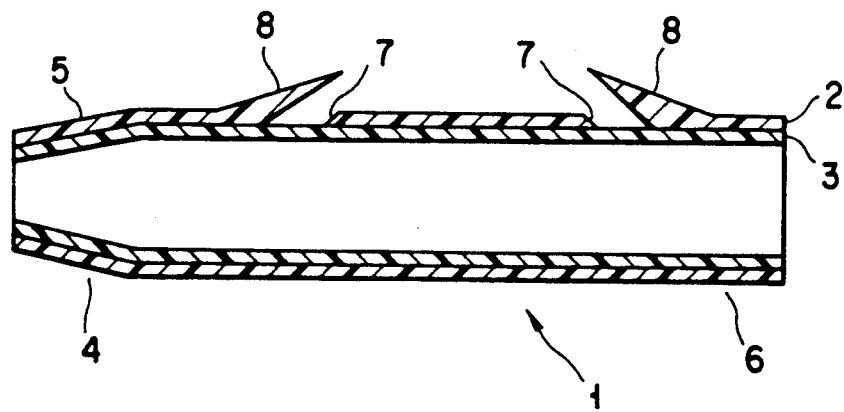
FIG. 10 shows a cross-sectional view showing a conventional stent tube for use in a human body cavity.

The fourth embodiment performs the same function as that of the first embodiment and has an advantage as will be set out below. Since the drainage tube 15 has the ribbon 16 disposed between the outer tube 2 and the inner tube 3, the drainage tube 15 is hard to collapse and flexible throughout the length. It is thus possible to freely vary the shape of the drainage tube 15. Since the shape of the drainage tube 15 can be varied in accordance with the state of a region of interest of a human being, if, as shown in FIG. 9, the drainage tube 15 is inserted from, for example, the duodinal papilla 17 into the general bile duct 18 and stays at that narrow duct, it is possible to retain the drainage tube after it has been bent, by fingers, etc., into an ideal configuration corresponding to the curve of the bile duct as shown in FIG. 8.

According to the aforementioned embodiment, the drainage tube is hard to bend, and is not collapsed, because of the presence of the reinforcing member between the outer tube and the inner tube. Since there is no possibility of the inner tube being broken in spite of the inner tube being made practically as thin as possible, it is possible to thicken the outer tube to a corresponding extent. Further, the side flaps can be made thickened and provide a firm elastic structure and, hence, the resultant tube structure provides a force of firm anchoring to the inner wall of the duct of the human being. After the three-layered structure has been assembled for a drainage tube, it can be cut by a cutter to provide side flaps. At that time, the reinforcing member of the drainage tube serves as a stopper and the side flaps can properly be formed on the outer tube only at a low cost. Further, it is easier to impart a contrast density providing ability to the braid in which case the front, together with the contract medium-bearing outer tube, performs the same function as a contrast medium.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A stent tube for medical use which is placeable in a duct of a human being to provide a passage, said stent tube an outer tube formed of a resin;

said outer tube having at least one flap formed thereon, as a raised cut area for providing a firm area of anchoring to an inner wall of a human body cavity;

an inner tube formed of a fluorine-based resin that has a frictional resistance that inhibits deposition of a foreign matter thereon; and a mechanically reinforcing member positioned between the inner tube and the outer tube for mechanically protecting the inner tube from damage when the at least one flap is formed on the outer tube.

2. The tube according to claim 1, wherein the mechanically reinforcing member includes means for firmly connecting the inner tube to the outer tube.

3. The tube according to claim 1, wherein the mechanical reinforcing member includes a multi-recessed surface that is set to be in biting contact with at least a surface of one of the inner and outer tubes.

4. The tube according to claim 1, wherein the mechanically reinforcing member comprises a braided cylindrical member formed of a plurality of braiding wires.

5. The tube according to claim 1, wherein the mechanically reinforcing member comprises a tightly wound wire coil.

6. The tube according to claim 1, wherein the mechanically reinforcing member comprises a coarsely wound wire coil.

7. The tube according to claim 1, wherein the mechanically reinforcing member comprises a flexible member that includes a spirally coiled metal ribbon.

8. The tube according to claim 1, wherein the outer tube comprises a polyethylene material and the inner tube comprises a fluorinated ethylenepropylene copolymer material.

9. The tube according to claim 1, wherein at least two flaps are formed on the outer tube.

* * * * *